United States Patent [19]

Palitzsch et al.

[11] Patent Number: 5,185,443
[45] Date of Patent: Feb. 9, 1993

[54] METHOD FOR PREPARING 5-CARBAMOYL-5H-DIBENZ[B,F]AZEPINE

[75] Inventors: Peter Palitzsch; Rainer Müller, both of Dresden; Erhard Richter, Radebeul, all of Fed. Rep. of Germany

[73] Assignee: Arzneimittelwerk Dresden GmbH, Radebeul, Fed. Rep. of Germany

[21] Appl. No.: 724,108

[22] Filed: Jul. 1, 1991

[30] Foreign Application Priority Data

Jul. 5, 1990 [DD] German Democratic Rep. ... 342510

[51] Int. Cl.$^5$ ............................................. C07D 223/20
[52] U.S. Cl. .................................................... 540/589
[58] Field of Search ......................................... 540/589

[56] References Cited

U.S. PATENT DOCUMENTS 2,762,796  9/1956  Morel et al. ..................... 540/589

FOREIGN PATENT DOCUMENTS 82719   6/1971  German Democratic Rep. .................... 540/589
264115  1/1989  German Democratic Rep. .................... 540/589

Primary Examiner—Robert T. Bond
Assistant Examiner—E. C. Ward
Attorney, Agent, or Firm—Schweitzer Cornman & Gross

[57] ABSTRACT

A process for producing carbamazepine

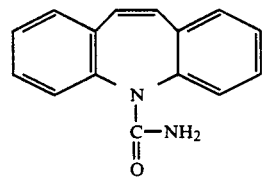

by (i) optionally purifying a solution of CCDA

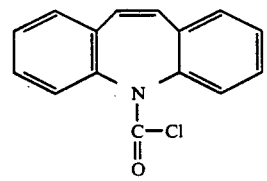

in an anhydrous, aromatic solvent; (ii) if required distilling off water in the solution; (iii) diluting the water-free solution with an additional amount of the anhydrous, aromatic solvent; (iv) in a reactor aminating the diluted solution at from about 70° C. to about 105° C. with an excess of ammonia to form a mixture of carbamazepine and ammonium chloride; (v) before completion of the amination introducing from about 10% to about 40% wt based on the solution of water into the mixture to obtain a crystal structure which facilitates stirring and thus completion of the amination; (vi) completing the amination by continuing the introduction of ammonia gas until the substantially complete conversion of CCDA to carbamazepine; (vii) separating crystalline carbamazepine/ammonium chloride mixture; (viii) dissolving ammonium chloride in the mixture with water; and (ix) recovering the crystalline carbamazepine which remained solid.

12 Claims, No Drawings

METHOD FOR PREPARING 5-CARBAMOYL-5H-DIBENZ[B,F]AZEPINE

FIELD OF THE INVENTION

The invention relates to a process for preparing 5-carbamoyl-5H-dibenz[b,f]azepine ("carbamazepine") of formula III,

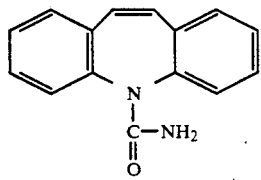

(III)

which is especially useful as an anti-epileptic agent. The process of the present invention is particularly suitable for the industrial scale manufacture of carbamazepine.

BACKGROUND OF THE INVENTION

The preparation of carbamazepine of formula III from iminostilbene or 5H-dibenz[b,f]azepine ("iminostilbene") of formula I

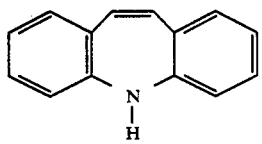

(I)

was described for the first time by W. Schindler in e.g. German accepted patent application No. 1,136,707, and in Swiss patent No. 54,023.

According to this method, the iminostilbene is suspended in toluene. Phosgene is introduced into this suspension, and the reaction mixture heats up to 70° C. Then, the reaction mixture is refluxed during the further addition of phosgene and is kept at boiling until the iminostilbene completely reacted and the evolution of hydrogen chloride has ceased. The introduction of phosgene is discontinued as soon as the reaction solution is free of iminostilbene. Excess phosgene is removed from the reaction mixture with dry nitrogen, or dry air, such as is described in German accepted patent application No. 1,001,271, in which the excess phosgene is blown out with dry air at the end of the phosgenation of 5H-10,11-dihydro-dibenz[b,f]azepine or iminodibenzyl. The so detoxified reaction solution is worked up conventionally and the resulting 5-chlorocarbonyl-5H-dibenz[b,f]azepine ("CCDA") of formula II

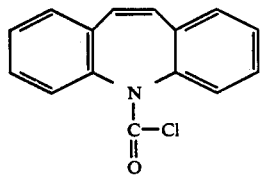

(II)

is recovered by crystallization, and is aminated in a known manner to the carbamazepine end product of formula III.

The known methods of preparation are all carried out in an inert, anhydrous solvent at temperatures above 100° C., such as in toluene, chlorobenzene, or o-dichlorobenzene (see, for example, the various publications summarized by B. Renfroe, et al. in Heterocyclic Compounds, Vol. 43, Azepines, part I, John Wiley & Sons Publisher, New York, 1984, page 524, table 118).

The dissociation of the iminostilbene hydrochloride formed by the phosgenation, into hydrogen chloride gas and free iminostilbene is carried out in all industrial processes by heating the reaction mixture to the boiling point in the neutral solvent and passing in phosgene under reflux conditions.

All high temperature phosgenations, carried out in the prior art, are conducted at 100° C. and higher, to achieve a complete phosgenation of the iminostilbene, or of the iminodibenzyl.

The known processes for preparing carbamic acid chlorides from secondary amines are summarized in a table in the organic chemistry methodology manual of Houben-Weyl (vol. E 4, pages 46–50, Georg Thieme Verlag, Stuttgart, New York City, Publisher, 1983). In these processes most often aromatic hydrocarbons, such as benzene, toluene or chlorobenzene, are used as solvents.

If the synthesis is carried out at low temperatures, when the phosgene is passed into a solution of the secondary amine, only half of the amine is converted into the desired carbamic acid chloride because the hydrogen chloride released during the reaction converts the other half of the amine into the hydrochloride. The amine hydrochloride precipitates in crystalline form. Thus, the yield of carbamic acid chloride can even in the most favorable cases amount only to 50%.

Since the work of H. Erdmann, et al. (J. Prakt. Chem. (2), Vol. 56, 7, 1897), it is known that the conversion can be completed if an inert, anhydrous base, such as pyridine, is used in an at least equimolar amount.

According to the Houben-Weyl manual (see above), in addition to pyridine, also triethylamine and, of course, the amine itself that is to be reacted, are suitable as inert bases. The cold phosgenation becomes more costly, since at least equimolar amounts of the inert base are always required. The process is costly and is more cumbersome, because the amine hydrochloride has to be separated out for recovering the inert base. Therefore, the cold phosgenation in the presence of inert auxiliary bases is important only for the reaction of temperature sensitive secondary amines, which increasingly tend to undergo side reactions at the high temperatures of the hot phosgenation.

In industry, the reaction is suitably carried out at temperatures above 100° C. The Houben-Weyl manual states in this connection that "[A]dvantageously, the reaction mixture is heated to a temperature above 100° C. while further phosgene is introduced, and the entire amine chloride is converted into the carbamic acid chloride."

The hydrogen chloride gas released by this thermal dissociation, carries along appreciable amounts of phosgene. Therefore, the off-gas must be detoxified and destroyed in special off-gas apparatus. Such a procedure can seriously endanger the environment in the case of an accident, because of the danger presented by the extremely toxic nature of phosgene which is a gas under ambient conditions.

The procedure of hot phosgenation has, above all, the following serious disadvantages:

the burden of having to deal with large amounts of liberated hydrogen chloride off-gas including phosgene and the entrained solvent vapors, and the resulting environmental protection problems;

long reaction times of more than 18-24 hours in contact with highly corrosive media;

large expenditure of energy;

a number of side reactions and the dark coloration of the reaction product, which leads to a substantial decrease in the quality of the carbamazepine end product; and increasing formation of unwanted 9-methylacridine byproduct at temperatures above 90° C. which represents a contraction of the 7-membered ring of the iminostilbene.

Only at temperatures of from about 90° C. does the thermal dissociation of the iminostilbene hydrochloride into free iminostilbene and hydrogen chloride gas proceed sufficiently rapidly to achieve reaction times which are acceptable for industrial purposes. However, iminostilbene is a temperature sensitive amine. Therefore, iminostilbene is suitably phosgenated by the method of Schindler, described in the aforementioned German accepted patent application No. 1,136,707.

The process variant preferred by Schindler is dividing the phosgenation into two stages, a cold phosgenation stage resulting in an about 50% conversion in the first phase, and a hot phosgenating stage. Conversion carried out in a second stage has clear advantages over a direct single stage hot phosgenation, because the yields are appreciably increased in this manner, the side reactions that take place above 90° C. are suppressed, and the quality and color of the end product are improved. Nevertheless, the aforementioned disadvantages continue to exist in the second stage of the reaction, i.e. from the start of the heating to 90° C. and during the thermal dissociation of the iminostilbene hydrochloride until the end of the reaction.

An excess of phosgene is introduced into the reaction mixture to utilize the gentle reaction conditions of the first, the cold phosgenating stage as much as possible. A pressure surge can occur if the reaction mixture is heated subsequently to dissociate thermally the iminostilbene hydrochloride. This dangerous possibility is also mentioned in the Houben-Weyl manual (volume E 4, page 744).

When a pressure surge occurs, the spontaneously released hydrogen chloride gas also carries along appreciable amounts of phosgene. Therefore, the apparatus for destroying or detoxifying the off-gases must be sufficiently large to avoid the release of phosgene into the atmosphere.

The reaction is advisably carried out at temperatures of between 90° C. and 100° C. to suppress the unwanted side reactions and the formation of the methylacridine byproduct. The phosgenation proceeds sufficiently rapidly at this temperature. However, the partial pressure of the phosgene is appreciably increased at the higher temperature, compared to that of the cold phosgenation, therefore it is not possible to prevent the steady escape of large quantities of phosgene being carried along by the liberated hydrogen chloride. This can, of course, be also realized from the fact that appreciably less time is required for the conversion of the first half of the iminostilbene in the cold phosgenation stage, than for the conversion of the second half in the hot phosgenation stage.

The reaction solution has to be detoxified after the complete conversion of the iminostilbene. The excess phosgene is blown out of the reaction solution with dry nitrogen as a rule, or a portion of the solvent is distilled off until the reaction mixture is free of phosgene. This detoxification method has the disadvantage that phosgene can leak into the atmosphere if there are any leaks due to the high gas pressure in the apparatus. Therefore, in the long run there is a constant danger of atmospheric contamination by the escaping phosgene.

In addition to the method of directly phosgenating iminostilbene of formula I, other methods of preparing carbamazepine of formula III are known. These start out from 10,11-dihydro-5H-dibenz[b,f]azepine ("iminodibenzyl") of formula IV

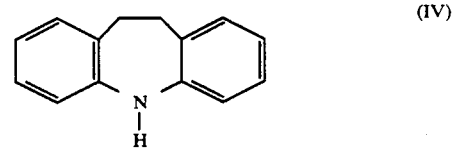

(IV)

In this connection see British patent No. 1,246,606 and East German patents Nos. 82,719; 100,948; 101,671; 102,149; 102,150; 102,151; 108,535; 133,052; 234,862 A1; and 234,863 A1. According to the methods described in these references, iminodibenzyl is reacted with phosgene in a boiling, inert, aromatic solvent, preferably toluene, or chlorobenzene. Phosgene is introduced into the refluxing material. Thus these methods also employ hot phosgenation with all of its attendant disadvantages.

The resulting 5-chlorocarbonyl-5H-10,11-dihydro-dibenz[b,f]-azepine of formula V

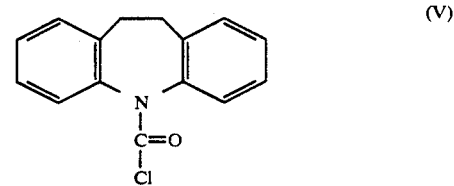

(V)

is reacted in an inert organic solvent with elemental bromine, or is otherwise subjected to selective bromination and the corresponding 10-monobromo derivative formula VI

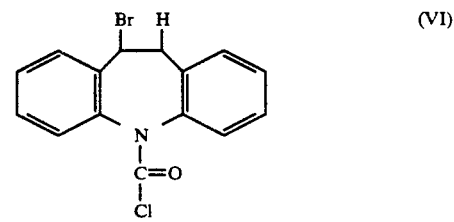

(VI)

and/or the 10,11-dibromo-derivative formula VII

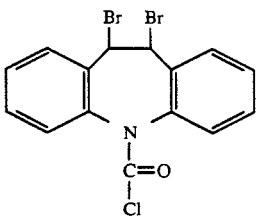

(VII)

is formed.

The bromo compounds of formulae VI and/or VII are subsequently dehydrobrominated and/or are thermally debrominated. A partial exchange (30–40%) of the chlorine atom of the 5-chlorocarbonyl group for a bromine atom takes place during such a thermal process. Due to the required high reaction temperatures (150° C.–170° C.) and because of the liberated bromine, these drastic reaction conditions necessarily lead to uncontrollable side reactions, such as bromination of the ring, resinification, cracking, and discoloration.

Thus the CCDA prepared by these processes contains, in addition to numerous, particularly bromine-containing, byproducts also some greasy, tarry, colored contaminants, the removal of which requires an undue effort.

The nature and structure of these byproducts is not known. The customary purification methods lead to appreciable losses.

No purification method was known until now, which can economically solve the problem of the residual bromine content. Thus, as determinedly high pressure liquid chromatography, the CCDA so prepared is present the average in an amount of 90%, and the precursor for the carbamazepine end product, contains about 10% impurities.

The CCDA intermediate prepared by the aforementioned methods can be recovered either by treating the hot solution with activated charcoal, filtering and isolating the product after crystallization or, after filtration, distilling off the solvent, and letting the melt of the product run into a precipitation bath of a different, suitable solvent, and then removing the crystallized product.

The so recovered CCDA intermediate is next aminated in a suitable solvent. Ammonia gas, liquid ammonia, concentrated aqueous ammonia, or ammonium salts in an aqueous solution can be used for the amination. The following amination methods are described in the literature.

According to the methods of the East German patents Nos. 82,719 and 102,150, Swiss patent No. 366,541, and German accepted patent application No. 1,001,271, the CCDA is partially or completely dissolved in ethanol or methanol. The resulting suspension or solution is treated with gaseous ammonia at temperatures, which are higher than the boiling point of the alcohol solvent, that is, the amination reaction is carried out under pressure in an autoclave. This is a technically manageable process, but a difficulty is presented by the fact that the alcohols are not inert, but react to an undesirable degree with the CCDA in a side reaction which cannot be suppressed. The corresponding esters are formed as byproducts of that undesired side reaction.

During the amination in methanol, regardless of whether the reaction is carried out under anhydrous conditions with gaseous ammonia, or with a concentrated aqueous solution of ammonia, about 1%–2% of a 5-carbomethoxy-5H-dibenz[b,f]-azepine byproduct is formed. This ester is not readily removed during the subsequent recrystallization of the crude carbamazepine end product. Even after two recrystallizations, the end product still contains about 0.1% of the 5-carbomethoxy-5H-dibenz[b,f]-azepine byproduct. Since according to the European Pharmacopoeia 2nd Ed., 1987, Part II, Fasc. 11, p. 543, Maisonneuve S.A. Publ., Saint-Ruffeine, France, the concentration of any single impurity may not exceed 0.01%, all amination methods in alcoholic solvents especially in primary, low molecular weight alcohol solvents lead to a carbamazepine, which does not meet the quality requirements. Therefore, these amination methods cannot be employed because they fail to satisfy the applicable quality requirements.

According to the method of East German patent No. 82,719, the amination can also be carried out in an inert aromatic solvent, (see Example 1, amination of 33.7 g of 5-chlorocarbonyl-10-bromo-iminodibenzyl in 500 ml benzene in an autoclave). This process variant has the advantage that esters cannot be formed, however, since the carbamazepine end product is formed is a polar compound, it is not readily soluble in benzene or toluene, even at elevated temperatures. Therefore, considerably more solvent is required to enable the stirring and mixing necessary for carrying out the indispensably quantitative conversion of the carbamic acid chloride. This results in the case of this process variant in a drastic drop in the yield for a given reactor size and reaction time.

According to the method of East German patent No. 264,115 A 3, the amination is also carried out in aromatic solvents, in that the solution of the 5-halocarbonyl-5H-dibenz[b,f]azepine is run into the aminating agent. A 15% to 25% aqueous solution of ammonia or aqueous ammonia, salt solution is used as aminating agent. Nonionic surfactants, or quaternary aryl-alkyl-ammonium salts are used as surface active materials, to enable working in a concentrated form. These materials are intended to insure better mixing and stirrability for achieving a quantitative conversion. Suitably, halogenated aromatic hydrocarbons, such as chlorobenzene, or bromobenzene, are used. It is noted that the trend is clearly towards methods that do not employ chlorinated hydrocarbons, to avoid contamination of the efficient and for more environmentally friendly operations.

All attempts failed to convert the method described in East German patent No. 264,115 A 3 with toluene as solvent, to a large scale, industrial production method. Benzene was not even considered for use as a solvent, because of its toxic tendency to product leukemia. After at most 1 hour in a conventional 3,200 liter vessel with an impeller stirrer run at 103 rpm, or with an anchor type stirrer, as the reactions proceeded, the reaction mixture could no longer be stirred. The reaction came to a halt long before the required complete conversion, because the precipitated carbamazepine rises to the top and forms an approximately 1 m thick, strongly coherent "crystalline cake", which can no longer be dispersed by stirring. The mass can be made stirrable within 1 to 2 hours by raising the temperature to about 105° C. to 110° C. under an increasing pressure in a closed system. However, as a consequence of the increase in temperature, the unreacted CCDA that is still present decomposes by hydrolysis. In this manner, up to 8% of the 5-chlorocarbonyl-iminostilbene reverts to the golden yellow starting material iminostilbene, and the carbamazepine end product becomes discolored. Purification is expensive and considerably increases the cost of production.

For the same reasons, it was also not possible successfully to convert to industrial scale production the method, proposed in East German patent application No. WP C07D/320613.5 (which is based on the method of East German patent application No. WP C07D/320612.7).

The amination process of East German patent No. 126,329 is the presently known and used method. According to this method, the isolated CCDA intermediate is introduced into butyl acetate and aminated with concentrated aqueous ammonia. Although this reaction takes place in a 2-phase system, the decomposition by hydrolysis of CCDA can also not be completely avoided in this case. A certain reverse reaction to the iminostilbene starting material, the extent of which varies with the reaction parameters selected, is always observed to take place.

Therefore, a need exists for a continuous, low cost, industrially upscalable method for preparing carbamazepine which meets the purity requirements of the European Pharmacopoeia.

DESCRIPTION OF THE INVENTION

The present invention is an economically feasible process for preparing carbamazepine of the required purity from CCDA on an industrial scale, under very gentle and mild reaction conditions in an almost quantitative yield, and of a significantly improved quality. The process of the present invention also includes a continuous method for producing carbamazepine from iminostilbene without isolating the CCDA intermediate, and without changing the solvent. The process of the present invention can be carried out within a significantly shorter reaction time and requires much less energy input. Furthermore, the invention achieves an improvement in the protection of the environment and therefore, is less dangerous than processes of the prior art. A subsidiary feature of the present invention also involves a new and improved process for making the CCDA intermediate from iminostilbene.

The process of the present invention prepares carbamazepine in a continuous process directly from the iminostilbene by employing a shorter reaction time, by avoiding the hot phosgenation phase, and excluding the previously customary thermal dissociation of the iminostilbene hydrochloride, while obtaining a quantitative yield and a significantly better quality.

Accordingly, the present invention comprises a process for converting a solution of 5-chlorocarbonyl-5H-dibenz[b,f]azepine (CCDA) in an anhydrous aromatic solvent to 5-carbamoyl-5H-dibenz[b,f]azepine (carbamazepine) by (i) first optionally removing any contaminants from the solution, (ii) if required distilling off water in the solution, (iii) diluting the water-free solution with an additional amount of the anhydrous aromatic solvent, (iv) aminating the solution at from about 70° C. to about 105° C. with an excess of ammonia gas to form a mixture of carbamazepine and ammonium chloride, (v) before the completion of the amination introducing from about 10% to about 40% based on the solution of water into the mixture to obtain a crystal structure which facilitates stirring and thus completion of the amination, (vi) completing the amination by continued introduction of ammonia gas until the conversion of CCDA to carbamazepine is substantially completed, (vii) separating crystalline carbamazepine/ammonium chloride mixture, (viii) dissolving ammonium chloride in the mixture with water, and (ix) recovering the crystalline carbamazepine which remains solid.

The foregoing conversion of CCDA to carbamazepine can be suitably carried out in a precursor stage by starting from 5H-dibenz[b,f]azepine (iminostilbene) without any separate recovery of the CCDA intermediate, in a continuous process, wherein the CCDA for the above mentioned conversion is prepared by (a) phosgenating an iminostilbene solution in an anhydrous solution in an anhydrous aromatic solvent at from about 20° C. to about 60° C. to form CCDA and iminostilbene HCl, (b) adding an aqueous base to the reaction mass to release the iminostilbene, (c) phosgenating the so released iminostilbene while maintaining an acidic environment, and (d) heating the mixture to of from about 80° C. to about 90° C. to self-detoxify the solution with the HCl that was formed. It is the resulting solution from the precursor stage process steps (a)–(d) which can then be suitably subjected to the final stage process steps (i)–(ix) for the preparation of the carbamazepine end product.

It is particularly suitable to prepare carbamazepine by the direct process combining the aforementioned process steps (a)–(d) and concluding with process steps (i)–(ix), without isolation of the CCDA precursor which is toxic to the skin.

The process steps (a)–(d) for preparing the precursor represent gentle and mild reaction conditions allowing obtaining the precursor in a quantitative yield and of a significantly better quality than has been possible in the prior art. The process also accomplishes its result in a significantly shorter reaction time and with appreciably lesser need for energy input. Furthermore, the hot phosgenation or thermal dissociation of the iminostilbene hydrochloride of the prior art process is avoided. Therefore, the process stage for the present invention for manufacturing the precursor is also environmental more safe. The reactions are conducted so that the emission of phosgene is eliminated and a self-detoxification of the reaction solution takes place. These objectives of the precursor manufacturing process stage of the present invention are accomplished by including phosgene or a solution of phosgene in an inert solvent, into a suspension of iminostilbene in the same kind of solvent at from about 20° C. to about 60° C. until the iminostilbene is converted into an almost equimolar mixture of CCDA and iminostilbene hydrochloride. Thereupon the iminostilbene is released from the thus formed iminostilbene hydrochloride, by the addition of an aqueous base, to make it available for complete phosgenation while maintaining an acidic reaction environment.

The reaction is suitably carried out at temperatures ranging from about 35° C. to about 50° C. After about 50% of the iminostilbene is reacted to produce the desired carbamic acid chloride, a dilute solution of an alkali hydroxide, or a dilute solution of ammonia water, or an aqueous solution of an alkali carbonate, or hydrogen carbonate, or of an alkaline hydrolyzing salt such as sodium acetate, is introduced into the reaction mass. The introduction of phosgene is maintained until a complete conversion of the iminostilbene, such as indicated by thin layer chromatography (TLC). During the inflow of the aqueous base, the temperature is maintained at from about 35° C. to about 50° C.

In the final phase of the phosgenation, the temperature is maintained at from about 40° C. to about 50° C., so that the carbamic acid chloride will not crystallize out. Temperature deviations of a few degrees up or down are of no consequence.

The introduction of phosgene is stopped as soon as iminostilbene can no longer be detected in the reaction solution. The strongly acidic reaction mixture of about pH 1 is next heated slowly to from about 80° C. to about 90° C. to hydrolyze the excess phosgene by the hydrochloric acid in the aqueous phase. The reaction mixture is detoxified in this manner in a significantly shorter time and more simply than it would be by the blowing-out method of the hot phosgenation process, which is carried out with the exclusion of water.

It is most surprising that in the precursor stage of the process of the present invention neither the CCDA already formed nor the phosgene, which is introduced, is decomposed to any noticeable extent by the added aqueous base, or by the aqueous hydrochloric phase which is present towards the end of the phosgenation. This is surprising, because as phosgene is detoxified, for example with a from about 15 to about 20% sodium hydroxide solution (as described for example in "Organikum", 6th edition, page 630, 1967 VEB Deutscher Verlag der Wissenschaften, Autorenkollektiv, Berlin), the CCDA as an alkali sensitive carbamic acid chloride, is also immediately and spontaneously converted in the presence of aqueous alkaline solutions by way of the sodium salt of the carbamic acid in question, and decarboxylation back into the iminostilbene.

It is for these reasons that the secondary amines cannot normally be reacted with phosgene in the presence of aqueous, alkaline solutions. Completely unexpectedly, however, the phosgenation of the iminostilbene proceeds significantly more quickly under the conditions described, which are clearly milder and more gentle. The reaction time is reduced by one half by the process of the present invention.

The formation of byproducts is also suppressed. Surprisingly, only very little 9-methylacridine is formed under the reaction conditions described. Pursuant to the process of the present invention this unwanted byproduct is removed in a very elegant way suitably after the "self-detoxification" and during the phase separation. The detoxified, hot reaction mixture is allowed to stand at from about 80° C. to about 90° C. for some time to permit the phases to separate. The lower, aqueous, strongly acidic phase is removed and discarded. Aside from the respective salt, this aqueous phase contains only about 0.2% of the originally used iminostilbene in the form of various byproducts. It is estimated that about 50% of these byproducts is 9-methylacridine, which is present as hydrochloride. Iminostilbene is present in an extremely small amount in the aqueous, acidic solution. Therefore, the detoxification of the reaction solution by the from about 7 to about 10% hydrochloric acid formed also has a positive effect in that amine-like, basic byproducts are extracted in the form of their hydrochloride from the organic phase, that is, the aqueous, acidic phase has a preliminary cleaning effect with respect to the carbamazepine end product.

Suitable as inert solvents are the aromatic hydrocarbons, benzene, toluene or chlorobenzene, as well as the chlorinated, aliphatic hydrocarbons, suitably chloroform, or carbon tetrachloride.

Suitably dilute alkali solutions or dilute ammonia water is used as the base. The use of such a suitable base assures a phosgenation which does not produce any off-gases until almost all of the iminostilbene is reacted, whereby only shortly before the end of the reaction does a slight decomposition of the introduced phosgene occur. This decomposition manifests itself in the evolution of carbon dioxide. The escaping carbon dioxide carries slight quantities of phosgene into the absorption receiver. However, compared to the known hot phosgenation method, these amount to only a small percentage of the phosgene- and HCl-containing off-gases, which are otherwise driven off and would have to be detoxified.

Pursuant to the precursor stage of the process of the present invention the equimolar amount of the hydrogen chloride released is chemically bound by the added base, while the rest is dissolved in the aqueous phase.

In principle it is also possible to use as the base aqueous solutions of alkali carbonates, or hydrogen carbonates. In this special case, however, the evolution of carbon dioxide commences immediately with the start of the inflow of these solutions into the reaction mixture, so that phosgene reaches the off-gas at the latest after a 50% conversion. Although even in this special case less phosgene is discharged than in the known hot phosgenation process, nevertheless the use of alkali hydroxide solutions or ammonia water is a more suitable base to be employed to the present process.

The use of the bases, however, is not possible at the start of the reaction, because the phosgene is immediately decomposed under alkaline conditions, that is, in the presence of an excess of aqueous solutions of base. However, almost neutral carbonates of low solubility, such as calcium carbonate, can be used already at the start of the phosgenation, initially in the form of an aqueous suspension as an acid collector. In this case, however, the evolution of carbon dioxide and the resulting expulsion of phosgene commence in an appreciably more timely manner, than when an aqueous solution of alkali carbonate is used after an about 50% conversion of the iminostilbene. Therefore, the aqueous solutions of the alkali carbonates or the aqueous suspensions of the alkali hydrogen carbonates or of the alkaline earth carbonates are not so desirable for large scale industrial phosgenations involving batches of up to or over 600 kg of iminostilbene.

However, in an embodiment of the precursor stage of the present invention, an aqueous suspension of the alkaline earth oxide, suitably of calcium oxide or magnesium oxide, or of an alkaline earth hydroxide is introduced after an approximately 50% conversion of the iminostilbene. For one equivalent of iminostilbene from about 0.55 to about 1.00 equivalents of base, but suitably only from about 0.55 to about 0.75 equivalents of base are used. For example, 0.55–0.75 moles of NaOH, KOH or $NH_3$ or 0.28–0.38 moles of CaO are required per mole of iminostilbene.

In a further embodiment of the precursor stage of the process of the present invention the inflow of the aqueous solution of the base is commenced already after about a from about 10 to about 20% conversion of the iminostilbene, but the rate of the introduction of the phosgene and the rate of adding the aqueous base are to be controlled so that the pH of the reaction mixture never strays into the alkaline region.

The solution of CCDA obtained in the precursor stage of the present invention can be optionally purified by once more extracting it with hydrochloric acid diluted with an equal volume of water and, after the separation of the phases, buffered to pH 5–6 and then optionally treated either at the end of the precursor stage, or at the beginning of the final stage, with an adsorbent, such as activated charcoal and/or aluminum oxide.

Either at the end of the precursor stage of at the beginning of the final stage, the CCDA solution, suitably in toluene which is optionally filtered to remove the optional activated charcoal, is dehydrated by azeotropic distillation in a water separation stage. The dewatered solution of the carbamic acid chloride (CCDA) is supplemented or diluted with solvent, so that, in the case of toluene, CCDA ratio to solvent of 1:6 (kg/l) is maintained as a suitable preparation.

In the final stage ammonia gas is passed into the optionally filtered CCDA solution in toluene at from about 70° C. to about 105° C., the internal pressure is suitably maintained at from about 0.01 to about 0.50 MPa, and most suitably at 0.01 to 0.25 MPa. In the initial phase, the introduction of the gas is commenced at from about 70° C. to about 85° C. Since the reaction is exothermic, the temperature and the internal pressure increase with time. The reaction temperature and pressure can be controlled very well by briefly cooling with water. The internal pressure is increased towards the end of the reaction to from about 0.1 to about 0.25 MPa.

According to the method described in East German patent application No. WP C07D/320613.5, as the amination progresses the reaction mixture becomes more creamy and thicker, because the carbamazepine/ammonium chloride mixture, which is formed, is not very soluble in toluene even at higher temperatures such as to about 105° C. If stirring is stopped, the thick, creamy reaction mass fills the entire reaction vessel. The crystals remain suspended even after several hours, because at this consistency the conversion of the last 5% of the CCDA is slowed down appreciably towards the end of the amination reaction. The amination reaction cannot be completed in this manner to such an extent, that the carbamazepine is free of the CCDA precursor. However, the isolated, crude carbamazepine must be free of the carbamic acid chloride precursor, because the latter compound can no longer be removed during the subsequent final purification by recrystallization of the carbamazepine. The stringent quality requirements of the "European Pharmacopoeia" limit the concentration of a single impurity to a maximum of 0.01%.

On the other hand, when a very limited amount of water is added at this point pursuant to the process of the present invention this has a surprisingly and unexpectedly extremely advantageous effect on the overall stirring behavior and on the consistency of the reaction mixture. This is, because this measure triggers a further crystalline conversion and thus it beneficially affects the complete, final conversion of the CCDA precursor to the carbamazepine end product.

If from about 100% to about 110 of the theoretical amount of ammonia gas has been passed into the reaction vessel and then the ammonia supply is turned off, the temperature and internal pressure will no longer change significantly. The last from about 1% to about 5% of CCDA does not produce an appreciable exothermic effect. The impressed ammonia gas reacts only extremely slowly due to the creamy, thick condition of the reaction mass.

However, if for example, about 25% by weight of water based on the CCDA is added at from about 85° C. to about 95° C., the reaction mixture becomes visibly less viscous and more easily stirrable within a very short time. If the stirrer is turned off, the crystals sink below the surface and the toluene solution separates within a short time into a clear upper phase. Surprisingly, the temperature of the reaction mixture also drops considerably, far more than could be calculated from the addition of the limited amount of water. It is assumed that there is an endothermic crystalline transformation.

A sandy, crystalline material is formed from the thick, creamy reaction mass, which is so heavy, that it forms a sediment when the stirrer is turned off. Due to the stirring conditions, which are significantly improved and facilitated after the addition of a little water, and the highly fluid consistency of the reaction mixture, it is now possible easily to complete the conversion reaction.

From about 10% to about 20%-25% excess of ammonia gas, based on the theoretical amount required, is forced into the reactor. The reaction mixture is subsequently stirred for a further from about 3 to about 5 hours at from about 80° C. to about 95° C. Towards the end of the post-reaction period, the pressure in the reactor is released through an absorption apparatus, the reaction mixture is degassed under reflux at the initial azeotropic boiling point of about 82° C., at a temperature somewhat lower than expected because of the escaping ammonia gas, and the reaction is allowed to go to completion. The end point is monitored and determined by TLC by comparing the cooled, clear toluene mother liquor to a solution of CCDA in toluene. There should not be more than about 1% of CCDA in the toluene mother liquor, that is, the conversion should be at least 99% of the theoretical.

The carbamazepine end product filtered off at this point generally does not contain any of the CCDA precursor.

At the end of the amination reaction, the reaction mixture is cooled. If the crude carbamazepine is filtered off with suction, it is surprisingly observed that the toluene mother liquor is dry in spite of the earlier addition of the water. No aqueous phase can be found below the toluene. It follows from this that the crystalline material which has been rather easily filtered off with suction is a crystalline mixture of carbamazepine and ammonium chloride, which completely binds the added water.

The crystalline material mixture advantageously repels toluene. Thus, when the mixed crystalline material is stirred with from about 5 to about 8-fold the amount of water at from about 50° C. to about 60° C. for several hours, the ammonium chloride dissolves out of the crystalline mixture, while some or all of the crude carbamazepine will swell up. However, upon cooling, the carbamazepine can be readily stirred and filtered off with suction, or very well centrifuged out out of the aqueous ammonium chloride solution. No toluene phase can be observed in the aqueous ammonium chloride solution after the separation of the carbamazepine. This separation of the two solvents, toluene and water, which is practically quantitative, is an advantageous feature in any large-scale industrial process application of the present invention.

Pursuant to the method of the present invention, suitably 3,200 liter or larger stirred reactor vessels can be used with impeller stirrers, suitably at about 100 rpm, with an internal diameter of about 1,600 mm, and a height of about 2,150 mm.

In contrast to the process of the present invention, all attempts failed completely to aminate a solution of CCDA by the methods described in the East German patent No. 264,115 A3 and in East German patent application No. WP C07D/320613.5 in the same size stirred vessel with the impeller stirrer with 110 l concentrated aqueous ammonia per 100 kg of CCDA, as well as with ammonia gas alone, when water is excluded a thick reaction mass is obtained, which cannot be stirred well at all, and which is not movable or well stirrable with an impeller stirrer, or with an anchor stirrer in a stirred vessel of the aforementioned size. Therefore, the essential requirement of at least 99% conversion could not be obtained by the prior art.

The present invention is further disclosed by the following illustrative examples.

EXAMPLE 1

255.7 g (1.0 mole) CCDA is suspended in from 1,400 to 1,500 ml toluene. The suspension is stirred and heated to from about 80° C. to about 90° C. Ammonia gas is passed into the hot solution while the reaction vessel remains closed. The ammonia gas immediately reacts by formation of carbamazepine and ammonium chloride. The introduction of the gas is regulated so that, on a laboratory scale, the pressure does not substantially exceed 1.0 kPa.

Precipitation of the carbamazepine commences after 30 minutes. After about 1 hour, the mixture is highly crystalline, but can still be stirred well. In the course of the next 30 to 60 minutes, the suspension becomes increasingly thick and more difficult to stir. The suspension assumes the consistency of cottage cheese. In the laboratory, a sword-shaped stirrer or a turbine stirrer stirs the mass only in the center. After about 100% of the theoretical amount of ammonia has been introduced, stirring is continued for 1 hour at 80° C. to 95° C. Then 100 ml water is added at about 90° C. The introduction of ammonia is continued, and the temperature in the reaction mixture is maintained at 80° C. to 85° C.

After about 30 minutes to 1 hour, the suspension with the cottage cheese-like consistency becomes increasingly more stirrable. A sandy, heavy crystalline modification is formed, which sinks when the stirrer is turned off. Under these conditions, at least 99% of the CCDA which is in solution becomes converted to carbamazepine within about 3 to about 5 hours. TLC is used on the clear toluene solution which is formed as the upper phase when the stirrer is turned off, to determine the end point of the reaction. At the end of the amination, the reaction mixture is cooled to from about 15° C. to about 20° C. The carbamazepine formed is a sandy, crystalline material mixture with ammoniumchloride which is then filtered off with suction.

The moist crystalline mixture of carbamazepine and ammonium chloride is subsequently stirred into about 1,000 ml water at about 50° C. to about 60° C. After cooling the carbamazepine is filtered off with suction. The crystalline cake is washed one or twice with water and then dried.

The yield is 228 to 235 g of crude, beige- to cream-colored carbamazepine at from about 96.5% to about 99.5% of the theoretical yield, having melting point of from about 190° to about 192° C.

The crude carbamazepine can suitably contain up to about 1% ammonium chloride. The salt can readily be removed by recrystallization from a mixture of methanol and water.

After concentrating by distillation of the water free toluene mother liquor, a further from about 4.4 to about 4.5 g of carbamazepine is obtained which is approximately from about 1.8 to about 1.9% of the theoretical yield. This material is contaminated with CCDA, 9-methylacridine, and by further unknown byproducts. The residue from the toluene mother liquor is collected. A larger quantity of the residue can either be processed to carbamazepine by further amination, or returned by hydrolytic splitting with potassium hydroxide solution to the iminostilbene starting material.

After an appropriate purification, the iminostilbene so obtained can be used once more in the phosgenation process.

EXAMPLE 2

200 kg (0.78 moles) CCDA is suspended in 1,200 l toluene in a 2,000 l stirred vessel with an anchor stirrer adapted to be rotated at 63 rpm. The suspension is stirred and heated to about 80° C. The passing in of ammonia is commenced as soon as there is a clear solution. The temperature of the reaction mixture increases as a function of the rate of addition of ammonia to from about 95° C. to about 105° C. The overpressure in the reactor is between from about 0.01 and about 0.15 MPa, depending on the temperature and the rate of addition of the ammonia. After 30 kg ammonia have been introduced, stirring is continued for 1 to 2 hours at from about 80° C. to about 100° C.

Then, 50 l water is added at from about 80° C. to about 85° C., and a further 2 to 5 kg of ammonia are forced in. Stirring is continued for a further hour at from about 80° C. to about 85° C. The reaction mixture becomes visibly more easily stirrable. The reaction mixture is kept under reflux for a further 2 to 5 hours to complete the amination.

The suspension is cooled and centrifuged after the end point was positively determined by TLC. The product is washed once with toluene in the centrifuge. The yield is 331 kg of crude product of carbamazepine, ammonium chloride, and water as the moisture left in the product after centrifuging.

The moist, crude product is stirred in 1,000 l water at from about 50° C. to about 60° C. After cooling, the carbamazepine is separated by a centrifuge. The product is washed with water while still in the centrifuge. The yield is 240 to 255 kg of centrifuge dry moist crude carbamazepine which when dried yields 180 kg that is 97.4% of the theoretical yield. The melting point is between about 189° C. and about 192° C.

A further 3 to 4 kg of crude carbamazepine that is 1.6% to 2.2% of the theoretical yield is obtained from the toluene mother liquor.

EXAMPLE 3

230 kg (0.9 kmoles) of CCDA is suspended in 1,200 l toluene in a 1,600 l stirred vessel having an impeller stirrer adapted to rotate at 125 rpm. Ammonia is metered into the about 85° C. hot solution. After 20 kg of ammonia was passed in, the reaction mixture is already quite thick due to the precipitated carbamazepine/ammonium chloride mixture. The temperature increases without heating to from about 102° to about 105° C. and the pressure increases up to one atmosphere overpressure. A total of from about 37 to about 38 kg of ammonia is passed in. Stirring is continued for a further from about 1 to about 3 hours at from about 85° C. to about 95° C.

The pressure is relieved through an absorber. 50 l water is added at from about 80° C. to about 85° C. The suspension becomes more stirrable within one hour.

The mixture is lightly stirred for a further from about 2 to about 5 hours. The end point of the conversion is determined with TLC. The product is worked up as in Example 2. The yield is from about 204 to about 208 kg of dry, crude carbamazepine, which is 95.5% to 98% of the theoretical yield. The melting point is between about 189° C. and about 191° C.

EXAMPLE 4

230 kg (0.9 kmoles) CCDA is suspended in 1,200 l toluene in a 1,600 l stirred vessel with impeller stirrer adapted to rotate at 125 rpm and aminated at from about 85° C. to about 105° C. with ammonia under pressure. The procedure is the same as is employed in Example 3. The pressure can rise to about 0.3 MPa.

After the introduction of from about 37 to about 38 kg of ammonia, stirring is continued for a further hour at from about 85° C. to about 105° C. Thereafter the reaction mixture is cooled to about 80° C. and the pressure is released into an absorber. At about 80° C., 50 l of a from about 10 to about 15% solution of ammonia in water is added. Within 1 hour, the added water causes a transformation of the crystalline structure. The reaction mixture is then held for a further from about 2 to about 5 hours until the conversion is completed at a temperature where it refluxes slightly. The azeotropic boiling point is somewhat reduced by the ammonia. An absorber is employed. The product is worked up as described in Examples 2 and 3. The yield is 200-208 kg of dry, crude carbamazepine, which is from about 93.5% to about 98% of the theoretical yield. The melting point of the product is 189° C.-192° C.

The rest of the product can be isolated from the toluene mother liquor, as in Example 1.

EXAMPLE 5

300 kg, (1.56 kmoles) iminostilbene is suspended in 1,500 l toluene in a 3,200 l stirred vessel with impeller stirrer adapted to rotate at 100-125 rpm, and is phosgenated at from about 35° C. to about 40° C. in an exothermic reaction. The temperature is maintained by cooling, at 40° C.-50° C. The color of the initial iminostilbene vanishes and there is no further exothermic heat generated after a few hours. After the addition of a dilute solution of a base, more phosgene is added. When the reaction has turned completely white, carbon dioxide evolves and a white foam is formed. TLC indicates a completion of the conversion to CCDA.

Introduction of phosgene is stopped and the reaction mass is heated to 80° C.-90° C. The reaction mixture is now free of phosgene due to its hydrolytic decomposition. The mass separates into two phases. The lower aqueous acidic phase is separated and discarded.

After removal of the aqueous phase, the pH of the toulene phase is buffered at a value of 5 to 6, and the water is removed by azeotropic distillation.

The hot CCDA solution is then diluted with further toluene so that the approximately 400 kg of CCDA that was formed is present in 2,300 to 2,500 l toluene and is then treated with about 5 kg of activated charcoal. The carbon-free filtered solution is aminated and worked up in a stirred vessel with an impeller stirrer at from about 80° C. to about 105° C. under a pressure of from about 0.01 to about 0.25 MPa, according to the method of Examples 2 to 4.

The dry, crude carbamazepine is washed until it is free of salt and is separated with a suction filter that is incorporated in the stirred reactor vessel. The yield is 337 to 350 kg of dry, crude carbamazepine, which is from about 94.4% to about 98% of the theoretical yield. The melting point is from about 189° C. to about 190° C.

EXAMPLE 6

160 Grams (0.835 moles) iminostilbene are suspended in 800 ml toluene. This suspension is heated to 35° C.-40° C. Phosgene is passed into the stirred suspension. The reaction is slightly exothermic. The temperature of the reaction mixture rises to approximately to 50° C. For industrial scale batches, the temperature of the reaction mixture is maintained at 40° C.-50° C. by cooling.

When about 50% of the iminostilbene is converted to the CCDA after a reaction time of about 1.5 hours, the temperature of the reaction mixture no longer rises and the iminostilbene color has disappeared. The slow addition of dilute sodium hydroxide solution (20 g of NaOH, or 0.50 moles, dissolved in 150 ml water) is commenced at this time, while steadily continuing to introduce more phosgene. The addition of the sodium hydroxide solution is concluded after 30-45 minutes. The iminostilbene hydrochloride goes into solution. More phosgene is passed into the solution.

As the reaction progresses, the reaction solution steadily assumes a brighter color. Towards the end of the reaction, the color of the foam of the reaction solution changes from yellowish brown through yellow to white. This white head of foam on the stirred reaction solution and the incipient evolution of carbon dioxide shortly before the end of the reaction are important indications that the conversion of iminostilbene is completed.

Towards the end of the reaction, the temperature is maintained at almost 50° C., so that the chlorocarbonyl-iminostilbene does not crystallize out. The introduction of phosgene is discontinued when iminostilbene can no longer be detected in the reaction solution. Water (100 ml) is added to keep in solution the NaCl that was formed.

The reaction mixture, which has a pH of 1, is then heated slowly from about 50° C. between about 80° C. and 90° C. Any excess phosgene is rapidly decomposed hydrolytically under these conditions.

The lower acidic aqueous phase is removed and discarded as soon as the reaction mixture is free of phosgene. This aqueous phase has a cleaning effect on the CCDA formed, because it contains from about 0.2 to about 0.3 gram of several amine-like byproducts in the form of their hydrochlorides. It particularly contains 9-methylacridine. The amine-like byproducts can be liberated from the aqueous phase with NaOH. If required, the toluene phase can be extracted with dilute hydrochloric acid and then washed with water. After separating the phases once more, the toluene solution of the CCDA is distilled. After removal of the solvent, the remaining liquefied chlorocarbonyl-iminostilbene is precipitated in methanol. The methanolic suspension is cooled down and the crystalline chlorocarbonyl-iminostilbene is filtered off with suction and dried.

The yield is 197-200 g of CCDA (i.e. 93-94% of the theoretical yield); the melting point is 157° C.-158° C.; and purity, according to high pressure liquid chromatography (HPLC), is 99.8%-100%;

Purity according to thin layer chromatography (TLC) is 99.7%-99.9%.

A further 5-10 g of CCDA are obtained by concentrating the mother liquor. The total yield thus is 205-207 g, which corresponds to 96.5-97.5% of the theoretical yield.

The chlorocarbonyl-iminostilbene (CCDA), which is obtained from the methanolic mother liquor, can be collected and worked up separately.

EXAMPLE 7

160 Grams iminostilbene are dissolved in 800 ml of toluene. Phosgene is passed into this suspension at about 35° C. to about 40° C. as described in Example 1. After 50% conversion of the iminostilbene, the slow addition of 70 ml of 12.7% ammonia water (density of 0.95 g/cc at 15° C.; and containing 0.50 moles of $NH_3$) is commenced, the introduction of phosgene is steadily continued. The dilute ammonia water is added dropwise over a period of about 1 hour. The introduction of phosgene is continued until the iminostilbene has been completely reacted. Then the reaction solution is slowly heated from about 50° C. to from about 80° C. and about 90° C. and stirring is continued at this temperature until phosgene can no longer be detected. The detoxification requires about 1 hour. The detoxified reaction mixture is then mixed with 100 ml of water to dissolve the ammonium chloride. After that, 4 g of activated charcoal are added. The mixture is stirred for a further hour at 80° C.-90° C. and is subsequently filtered. The charcoal is washed with 50 ml of hot toluene. The aqueous, acidic phase is removed from the filtrate and discarded. The toluene solution is worked up as described in Example 6.

The yield is 195-205 g CCDA (i.e. 92.0-96.5% of the theoretical yield); the melting point is 157° C.-158° C.; and purity according to HPLC is 99.8%-100%.

A further 3-10 g of CCDA are obtained from the methanolic mother liquor by concentration.

EXAMPLE 8

160 Grams iminostilbene are suspended in 800 ml of chlorobenzene. This suspension is treated with phosgene as described in Example 6. After 50% of the iminostilbene is converted, the addition of dilute potassium hydroxide solution (30 g KOH or 0.55 moles, dissolved in 170 ml water) is commenced. This alkaline solution is added dropwise and uniformly over a period of about 45 minutes, while phosgene is continuously being introduced.

During phosgenation, the temperature is maintained at 35° C.-45° C., suitably at about 34° C. to about 40° C. Since CCDA is more soluble in chlorobenzene than in toluene, it is possible to carry out the reaction at 40° C. without having the reaction product crystallizing out. In toluene, the crystallization of chlorocarbonyl-iminostilbene (II) can be expected to occur at temperatures below 40° C. After the iminostilbene has completely reacted, the reaction mixture is detoxified as in Example with 6, or Example 7, with 80 ml of water being added to keep in solution the potassium chloride which was formed. The reaction mixture is then mixed with 4 g activated charcoal, stirred for 1 hour at 80° C.-90° C. and is then filtered.

The charcoal is washed with 50 ml of hot chlorobenzene. The aqueous phase is removed at 80° C.-90° C., if necessary, with the addition of a surface active material to break the emulsion layer, and is then discarded. The chlorobenzene phase is worked up as in Example 5.

The yield is 190-193 g of CCDA (i.e. 90-91.5% of the theoretical yield), the melting point is 157° C.-158° C.; and the purity according to HPLC is 99.75%-100%.

A further 10-15 g of CCDA are obtained from the methanolic mother liquor.

EXAMPLE 9

160 Grams iminostilbene are suspended in 800 ml chlorobenzene and treated with phosgene at about 35° C. to about 50° C. until the iminostilbene color disappeared. A solution of 41 g (0.50 moles) of sodium acetate in 150 ml of water is added dropwise over a period of one hour to the approximately equimolar mixture of CCDA and iminostilbene hydrochloride, while phosgene continues to be passed into the reaction mixture. The temperature of the reaction mixture may fall to 40° C. during this time. At about 40° C. to about 45° C. after the addition of the acetate solution, more phosgene is passed in until the iminostilbene has been completely converted. The reaction solution then is heated to from about 80° C. to about 90° C. and is detoxified. The phosgene-free reaction mixture is transferred to a separating funnel. After removal of the aqueous phase, in which the odor of acetic acid can be detected, the chlorobenzene solution is worked up as described in either one of Examples 6 to 8.

The yield is 192-194 g of CCDA (i.e. 90.5-91.5% of the theoretical yield); and the melting point is 156° C.-158° C.

EXAMPLE 10

160 Grams iminostilbene are suspended in 800 ml of toluene and reacted with phosgene as in Example 5. After 50% of the iminostilbene has been converted, the slow addition of 14 g (0.25 moles) of CaO in 170 ml water is commenced while stirring the suspension to keep it homogeneous. Phosgene continues to be introduced during this time. The addition of the CaO-water suspension takes place in about 45 minutes.

Phosgene continues to be introduced into the reaction mixture until all of the iminostilbene is reacted, while the temperature is maintained at 40° C. to 45° C., to the extent possible. The reaction mixture is detoxified in the usual manner and then worked up as described in Example 5.

The yield is 197-201 g of CCDA (i.e. 93-94.5% of the theoretical yield)

A further 5-10 g of CCDA are obtained by working up the methanolic mother liquor.

EXAMPLE 11

160 Grams iminostilbene are suspended in 800 ml toluene. The introduction of phosgene is commenced at 40° C. After 10-20% of the iminostilbene is converted, dilute sodium hydroxide solution (24 g NaOH or 0.60 moles, dissolved in 200 ml water) is slowly added. The rate of addition of the phosgene and the amount of dilute sodium hydroxide solution added are such that the pH of the reaction mixture during the addition of the sodium hydroxide solution should not stray into the alkaline region. The phosgenation is carried out at 40° C.-50° C. After the iminostilbene is completely converted, the reaction mixture is worked up as in Example 5.

The yield is 197-200 g of CCDA (i.e. 93-94% of the theoretical yield); and the melting point is 157° C.-158° C.

We claim:
1. A process for producing carbamazepine having the formula

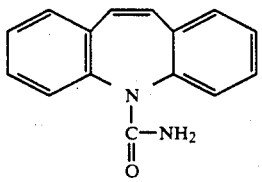

which comprises (i) optionally purifying a solution of CCDA having the formula

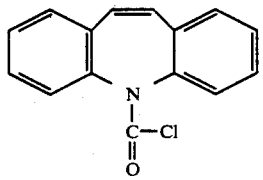

in an anhydrous, aromatic solvent; (ii) if required distilling off water in the solution; (iii) diluting the water-free solution with a additional amount of the anhydrous, aromatic solvent; (iv) in a reactor aminating the diluted solution at from about 70° C. to about 105° C. with an excess of ammonia to form a mixture of carbamazepine and ammonium chloride; (v) before completion of the amination introducing from about 10% to about 40% wt based on the solution of water into the mixture to obtain a crystal structure which facilitates stirring and thus completion of the amination; (vi) completing the amination by continuing the introduction of ammonia gas until the substantially complete conversion of CCDA to carbamazepine; (vii) separating crystalline carbamazepine/ammonium chloride mixture; (viii) dissolving ammonium chloride in the mixture with water; and (ix) recovering the crystalline carbamazepine which remained solid.

2. The process of claim 1, wherein said optional step (i) is carried out with a solid adsorbent, said step (i) further comprises removing said solid adsorbent from the solution.

3. The process of claim 2, wherein the solid adsorbent is activated charcoal.

4. The process of claim 1, wherein said step (ii) of dewatering, comprises azeotropically distilling water off the solution.

5. The process of claim 1, wherein said solvent is toluene, and said step (iii) comprises diluting said solution to a CCDA:solvent weight ratio of about 1: about 6.

6. The process of claim 1, wherein in said step (iv) the ammonia gas is introduced at an internal pressure of from about 0.01 to about 0.5 MPa.

7. The process of claim 1, wherein in said step (iv) the temperature is between about 70° C. and about 85° C., and the internal pressure is between about 0.01 and about 0.25 MPa.

8. The process of claim 7, wherein toward the end of the reaction the internal pressure is between about 0.1 and about 0.25 MPa.

9. The process of claim 1, wherein said excess of ammonia used in the reaction, is from about 10% to about 25%.

10. The process of claim 1, wherein said step (vi) further comprises stirring the reaction mixture for from about 3 to about 5 hours while continuing with the introduction of ammonia gas, and upon the substantial completion of the conversion, releasing the pressure from the reactor, and degassing the reaction mixture.

11. The process of claim 1, wherein said step (viii) comprises stirring the carbamazepine/ammonium chloride mixture in from about 5 to about 8-fold the weight of water at from about 50° C. to about 60° C. for several hours to dissolve the ammonium chloride out of the crystalline mixture.

12. A process for converting CCDA of the formula

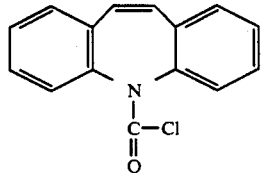

in an anhydrous, inert solvent, to carbamazepine of the formula

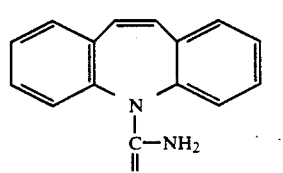

which comprises, (i) optionally contacting the solution with an adsorbent for removing impurities therefrom, and then separating said absorbent; (ii) substantially dewatering said solution by azeotropic distillation; (iii) diluting said solution by adding thereto a further amount of said solvent; (iv) introducing a stoichiometric excess of from about 10% to about 25% wt of ammonia into said solution at an internal pressure of from about 0.1 to about 0.5 MPa; (v) during the introduction of the ammonia, adding from about 10% to about 40% wt water into the solution, and then (vi) continuing the introduction of ammonia while stirring the solution for from about 3 to about 5 hours; (vii) separating the carbamazepine/ammonium chloride mixture formed during the reaction; (viii) dissolving the ammonium chloride from said separated mixture by stirring in from about 5 to about 8 fold the weight of water; and (ix) filtering and washing the remaining solid carbamazepine free from the dissolved ammonium chloride.

* * * * *